United States Patent
Kendall et al.

(10) Patent No.: US 9,927,329 B2
(45) Date of Patent: Mar. 27, 2018

(54) SIGNATURE COLLECTION CARTRIDGE WITH EMBOSSED COLLECTION SUBSTRATE

(71) Applicant: Signature Science, LLC, Austin, TX (US)

(72) Inventors: John Kirby Kendall, Cedar Park, TX (US); Robyn L. Guerrera, Austin, TX (US); Alec N. Van Tilburg, Austin, TX (US)

(73) Assignee: Signature Science, LLC, Austin, TX (US)

(*) Notice: Subject to any disclaimer, the term of this patent is extended or adjusted under 35 U.S.C. 154(b) by 44 days.

(21) Appl. No.: 14/694,768

(22) Filed: Apr. 23, 2015

(65) Prior Publication Data
US 2015/0308929 A1  Oct. 29, 2015

Related U.S. Application Data

(60) Provisional application No. 61/983,154, filed on Apr. 23, 2014.

(51) Int. Cl.
*G01N 1/20* (2006.01)
*G01N 1/22* (2006.01)

(52) U.S. Cl.
CPC .............. *G01N 1/20* (2013.01); *G01N 1/2214* (2013.01); *G01N 1/2273* (2013.01); *Y10T 436/255* (2015.01); *Y10T 436/25875* (2015.01)

(58) Field of Classification Search
CPC .. G01N 1/10; G01N 1/20; G01N 1/22; G01N 1/2214; G01N 1/2273; G01N 1/2294; Y10T 436/25; Y10T 436/25375; Y10T 436/255; Y10T 436/2575; Y10T 436/25875

USPC ....... 436/147, 167, 174, 177, 178, 180, 181; 422/68.1, 69, 88, 501
See application file for complete search history.

(56) References Cited

U.S. PATENT DOCUMENTS

| | | | | |
|---|---|---|---|---|
| 2,646,887 A | * | 7/1953 | Robinson | B01D 29/111 210/347 |
| 3,346,105 A | * | 10/1967 | Nye | B65D 65/403 24/DIG. 11 |
| 3,746,954 A | | 7/1973 | Lapp et al. | |
| 4,348,712 A | | 9/1982 | Newcomb | |
| 4,439,812 A | | 3/1984 | Chapman | |
| 5,382,774 A | | 1/1995 | Bruck et al. | |
| 5,551,278 A | * | 9/1996 | Rounbehler | G01N 1/02 436/156 |

(Continued)

OTHER PUBLICATIONS

Air Monitoring A Complete Line of Products for Air Monitoring; Supelco Analytical product brochure; sigma-aldrich.com/air monitoring; 2008; 52 pages.

(Continued)

*Primary Examiner* — Maureen Wallenhorst
(74) *Attorney, Agent, or Firm* — John A. Fortkort; Fortkort & Houston PC (57) ABSTRACT

A device (201) is provided for collecting signatures from an ambient fluid. The device includes a housing (205) equipped with an (207) inlet and an outlet (209) which are in fluidic communication with each other, and a signature collector (203) which has a plurality of spaced-apart layers (213). The signature collector is disposed in a fluidic flow path between the inlet and the outlet such that a flow of fluid passes through adjacent layers of the signature collector. Each of the layers includes a substrate (217) having a sorbent or adherent (219) disposed thereon, and a plurality of embossments (215) which maintains the layers in the spaced-apart configuration.

18 Claims, 6 Drawing Sheets

(56) References Cited

U.S. PATENT DOCUMENTS

| | | | |
|---|---|---|---|
| 5,608,968 A | 3/1997 | Maus et al. | |
| 5,874,153 A | 2/1999 | Bode et al. | |
| 6,477,905 B1* | 11/2002 | Mitra | G01N 30/00 |
| | | | 73/863.12 |
| 6,722,182 B1* | 4/2004 | Buettner | B01D 53/30 |
| | | | 422/305 |
| 6,892,795 B1* | 5/2005 | Steele | F23L 15/02 |
| | | | 165/10 |
| 7,014,688 B2 | 3/2006 | Griffiths et al. | |
| 7,096,749 B2 | 8/2006 | Schimmoller et al. | |
| 7,600,439 B1* | 10/2009 | Patterson | G01N 1/405 |
| | | | 73/23.37 |
| 2004/0050183 A1 | 3/2004 | Schimmoller et al. | |
| 2006/0123928 A1 | 6/2006 | Schimmoller et al. | |
| 2012/0109583 A1 | 5/2012 | Bartlett et al. | |
| 2013/0167941 A1 | 7/2013 | Bartlett | |
| 2013/0291623 A1 | 11/2013 | Perlinger et al. | |
| 2013/0306555 A1 | 11/2013 | Chattopadhyay | |
| 2013/0337477 A1 | 12/2013 | Kuhr et al. | |
| 2014/0004505 A1 | 1/2014 | Su et al. | |
| 2014/0026638 A1 | 1/2014 | Bowers, II et al. | |

OTHER PUBLICATIONS

Schultz, Kenneth J.; "Seri Desiccant Cooling Test Facility: Status Report; Preliminary Data on the Performance of Rotary Parallel-Passage Silica-Gel Dehumidifier"; Apr. 1986; 59 pages.

"Camsco Sorbent Selection Chart"; Carusco Agent Monitoring Supply Company; 2009; one page.

\* cited by examiner

SIGNATURE COLLECTION CARTRIDGE WITH EMBOSSED COLLECTION SUBSTRATE

This application claims the benefit of priority from U.S. Provisional Application No. 61/983,154, filed Apr. 23, 2014, having the same title, and having the same inventors, and which is incorporated herein by reference in its entirety.

FIELD OF THE DISCLOSURE

The present disclosure relates generally to devices for collecting signatures from ambient fluids, and more particularly to signature collectors which are equipped with a multi-layered collection substrate in which adjacent layers are maintained in a spaced-apart configuration.

BACKGROUND OF THE DISCLOSURE

Various sampling systems have been developed in the art to collect signatures of interest from air, water and other ambient fluids. Such systems are utilized, for example, to detect the emission of environmental pollutants at industrial sites, as part of environmental remediation efforts, or in the enforcement of chemical or nuclear arms treaties. Typically, such systems are designed to capture signatures of interest on a medium that is absorbent or attractive to signatures of interest. The captured signatures may later be desorbed, typically by heating the medium or through chemical extraction. The desorbed signatures may then be subjected to chemical, biological or radiological analysis. In the case of chemical signatures, for example, gas chromatography/mass spectrometry (GC/MS) is frequently utilized to analyze the signatures.

Alternatively, in some applications, the captured signatures may be caused to undergo a reaction to make a new signature that is more useful. For example, in some applications, formaldehyde and other aldehydes are reacted with 2,4-Dinitrophenylhydrazine (DNPH) to form stable hydrazones, which may be extracted from the silica gel and analyzed by liquid chromatography.

Sampling systems of the foregoing type may be active or passive. In active sampling systems, the fluid of interest (which may be, for example, ambient air or water) is actively pumped or drawn into or through the sampling media. By contrast, passive sampling systems typically rely on passive mechanisms for signature capture, such as the unassisted molecular diffusion of gaseous analytes through a diffusive surface onto an adsorbent medium. In many implementations, the sampling media is disposed in a stainless steel or glass tube equipped with an inlet and an outlet.

Various media may be utilized in the foregoing sampling systems. Generally, it is desirable for the sampling media to (a) provide an acceptable pressure drop during sampling, (b) exhibit sufficient capacity or breakthrough volume for the application to which the media is directed, (c) be suitably absorbent or attractive to signatures of interest under typical sampling conditions, (d) be capable of desorbing these signatures or otherwise permitting their analysis under suitable laboratory conditions, and (e) in the case of chemical signatures, to not interfere with the chemical fingerprint of the signatures in GS/MS or other commonly used analytical methods. Graphitized carbon black (GCB) of varying particle sizes is commonly used as a sampling media in sampling devices intended for use with organic chemical signatures, due to its affinity for common organic chemicals under sampling conditions and its ability to readily undergo thermal desorption of these materials. In a typical implementation, the GCB is disposed as a packed bed within a glass or stainless steel tube equipped with an inlet and an outlet.

SUMMARY OF THE DISCLOSURE

In one aspect, a device is provided which comprises (a) a housing equipped with an inlet and an outlet which are in fluidic communication with each other; and a signature collector which has a plurality of spaced-apart layers and which is disposed in a fluidic flow path between said inlet and said outlet such that a flow of fluid passes through adjacent layers of the collector. Each of the spaced-apart layers includes a (preferably embossed) substrate having a sorbent or adherent disposed thereon.

In another aspect, a method is provided for collecting a sample of a signature from an ambient fluid. The method comprises (a) providing a device comprising (i) a housing equipped with an inlet and an outlet which are in fluidic communication with each other, and (ii) a signature collector which has a plurality of spaced-apart layers and which is disposed in a fluidic flow path between said inlet and said outlet such that a flow of fluid passes through adjacent layers of the collector, wherein each of the spaced-apart layers includes a (preferably embossed) substrate having a sorbent or adherent disposed thereon; and (b) passing the ambient fluid through the device such that the signature is captured by the collector.

In a further aspect, a device is provided which comprises (a) a housing equipped with an inlet and an outlet which are in fluidic communication with each other; a wound substrate having a plurality of discrete embossings that maintain adjacent layers of the substrate in a spaced-apart relation to each other, wherein said substrate is disposed in a fluidic flow path between said inlet and said outlet such that the flow path extends through the spaces between adjacent layers in said substrate; and an adherent disposed on said substrate such that the adherent is in fluidic contact with said flow path

DETAILED DESCRIPTION

As used herein, the term "signature" refers to a chemical, biological, radiological or particulate material which is present in an ambient fluid (such as, for example, air or water) and whose capture is desired for analytical or transformative purposes. The term "analyte", as used herein, refers specifically to a chemical signature. A signature may be indicative of a chemical, biological or radiological event such as, for example, environmental contamination, the spread of a disease or infectious agent, or the infraction of a chemical or nuclear arms treaty. The term "transformative", as used herein, refers to a process in which a sorbent acts not only to capture a signature, but also to react and transform that signature into a more useful derivative signature (for example, (i) the conversion of an aldehyde into its hydrazone by reaction with DNPH, or (ii) the reaction of sorbed acetylene and alcohol to make a vinyl ether).

While the sampling systems developed in the art to date have many advantageous properties, these systems also suffer from some infirmities. In particular, as noted above, many of these systems feature a packed sorbent bed which is disposed within a glass or stainless steel tube equipped with an inlet and an outlet. The pressure drop across the sorbent bed is often significant and typically requires the use of a fan, pump or other fluid driving means to create a fluidic flow through the sampling media. Hence, sorbent beds of this type are typically limited to active sampling systems, and the size and power requirements of the fluid driving means are often somewhat proportional to the magnitude of the pressure drop.

While the pressure drop in a sampling system featuring a packed sorbent bed may be reduced through the use of larger particle sizes, this often has the effect of reducing the efficiency of the sampling media at capturing certain signatures of interest. This issue is further complicated by the need to provide suitable residence times for the ambient fluid in order for signature capture to occur, and the need (in some applications) to provide external heating of the packed bed for desorption of the signature.

There is thus a need in the art for a sampling system for signature capture which exhibits a reduced pressure drop compared to packed bed systems, which is amenable to use as an active or passive system, which (in the case of an active system) allows reductions in the size and/or power requirements of the fluid driver, and which provides sufficient residence times and affinities for signature capture to occur. It has now been found that these and other needs may be met with the systems, devices and methodologies disclosed herein.

In a preferred embodiment, a signature collector is provided which is equipped with a substrate that is coated with a sorbent or adherent. The substrate, which is preferably an embossed metal substrate, is wound, folded, or otherwise arranged into a multi-layered construct in which the adjacent layers are spaced-apart from each other (by virtue of the embossments or by other suitable means). Signature collectors of this type may be made which exhibit low pressure drops, and hence which allow for a reduction in the size of the device and/or in its power requirements. Moreover, signature collectors of this type may be made which exhibit acceptable residence times and affinities for signatures of interest, and which are useful in both active and passive systems.

Figure 1:
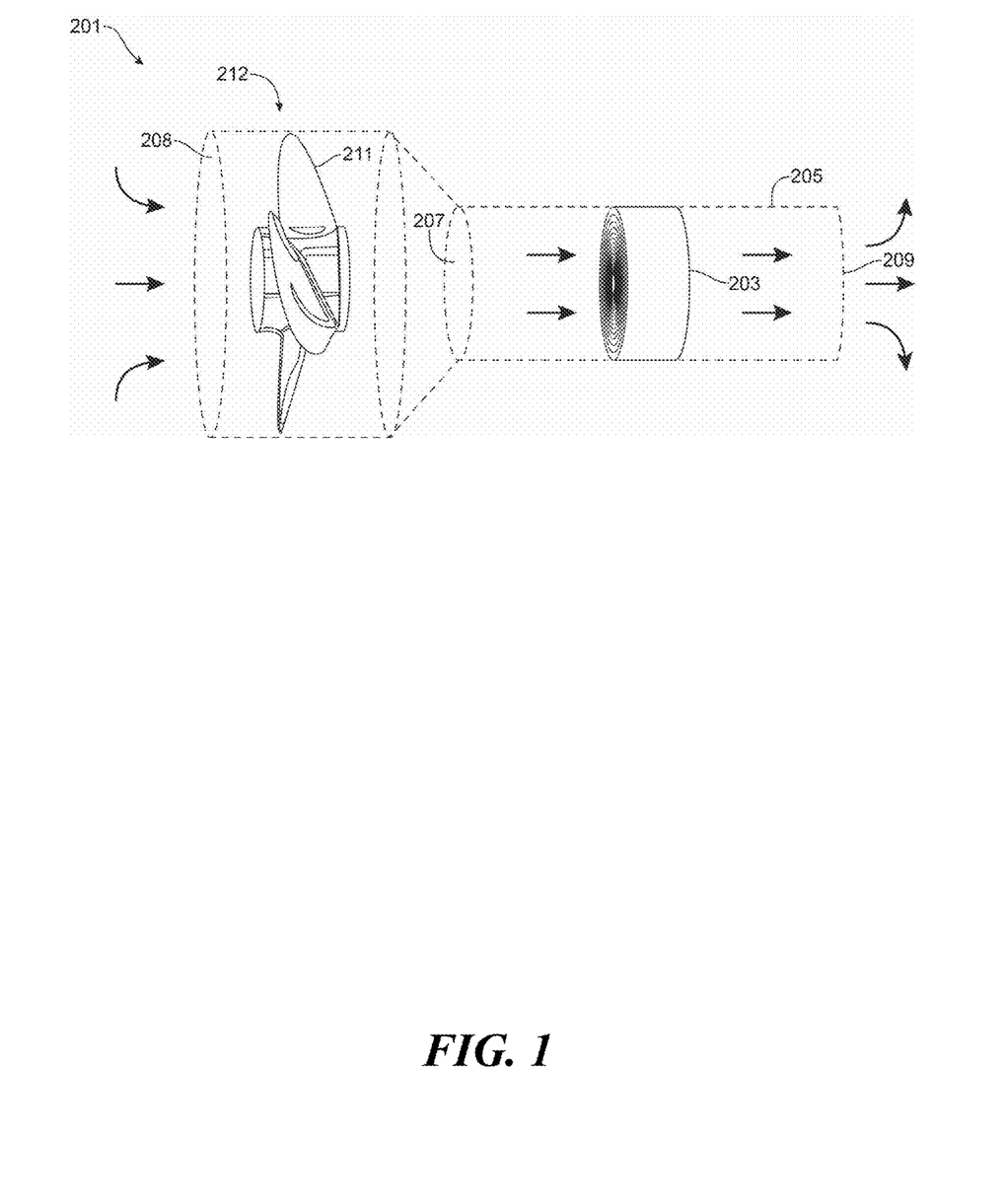
FIG. 1 is an illustration of a sampling device in accordance with the teachings herein.

FIG. 1 illustrates a first particular, non-limiting embodiment of a sampling device in accordance with the teachings herein. As seen therein, the sampling device 201 in this particular embodiment features a signature collector 203 which is disposed within a glass or stainless steel tube 205 equipped with an inlet 207 and an outlet 209. The sampling device 201 in this particular embodiment is equipped with a fan 211 disposed within a fan compartment 212. The fan compartment 212 is equipped with an inlet 208 and is adjacent to, and in fluidic communication with, the tube 205.

In use, an ambient fluid is drawn into the inlet 208 by the fan 211, passes through the signature collector 203, and exits the tube 205 by way of the outlet 209. Signatures of interest are trapped or otherwise captured in the signature collector 203, and may subsequently be analyzed through suitable chemical, biological, physical, or radiological analysis such as, for example, GS/MS, x-ray diffraction, microscopic examination, or the like.

Figure 2:
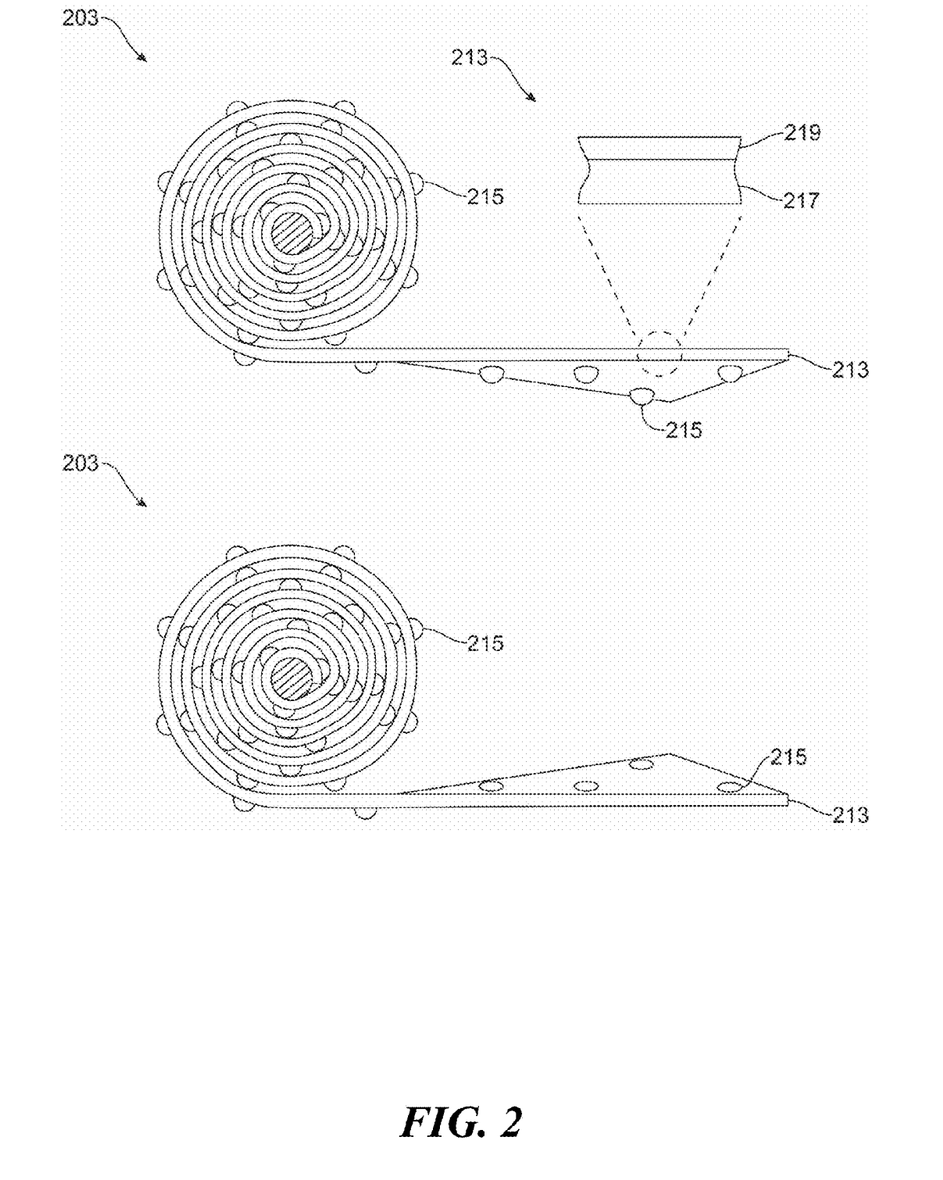
FIG. 2 is an illustration showing the details of the signature collector of the sampling device of FIG. 1.

FIG. 2 illustrates the signature collector 203 of FIG. 1 in greater detail. As seen therein, the signature collector 203 consists of a winding of a film 213 which is embossed with a plurality of protrusions 215. In a preferred embodiment, the film comprises a metal foil or other suitable substrate 217 which is coated with a sorbent or adherent 219. More preferably, the substrate 217 is coated on both sides with a sorbent or adherent 219. The dimensions of the protrusions are chosen such that, when the film 213 is wound, folded or otherwise assembled into a multi-layer construct, the protrusions 215 maintain adjacent layers of the film 213 in a spaced-apart arrangement which is conducive to fluidic flow between the adjacent layers and which reduces the pressure drop experienced by the fluidic flow (compared, for example, to a packed bed device). The dimensions and geometries of the protrusions are also chosen such that the mechanical properties (e.g., the tensile strength and modulus) of the film are not sufficiently reduced so as to impair winding or handling of the film.

Of course, it will be appreciated that the signature collector 203 may be adapted to a wide range of uses and may be used, for example, to collect a variety of chemical, biological, physical or radioactive signatures. Hence, the particular construction of the film 213 (including the identity of any absorbent or adherent utilized) may be adapted to a particular signature of interest as dictated, for example, by the intended use of the sampling device 201.

The systems, devices and methodologies disclosed herein may be further understood with reference to the following particular, non-limiting examples.

Example 1—Embossing Height

A one-inch wide aluminum foil (5052-H19 alloy) having a thickness of 50 microns was embossed with rollers possessing embossing teeth of differing densities. For this set of experiments, the three teeth densities studied had 16, 30 and 60 teeth per inch (TPI) counts. The embossing pressure was varied so that maximum embossing height was obtained without excessive puncturing of the foil. However, puncturing of the foil was not found to negatively impact the performance of the cartridge at the teeth densities and dimple heights investigated. It was observed that, as TPI increases, dimple height decreases at optimal spacing. The maximum dimple height was observed to be approximately 210 microns, which resulted when using 16 TPI knurls.

Example 2—Aluminum Alloys

Several different commercial aluminum foils were compared to determine their ability to emboss. In each case, a 1-inch wide piece of the foil was embossed using the 16 TPI embosser. The dimple height for commercially available aluminum alloys is set forth in TABLE 1 below.

TABLE 1

Dimple Height for Various Foil Thicknesses

| Alloy | Foil Thickness (microns) | Embossing Height (microns) |
| --- | --- | --- |
| 5052 H19 | 30 | 140 |
| 5052 H19 | 50 | 141 |
| 5052 H19 | 50 | 147 |

TABLE 1-continued

Dimple Height for Various Foil Thicknesses

| Alloy | Foil Thickness (microns) | Embossing Height (microns) |
| --- | --- | --- |
| 1235 H19 | 50 | 156 |
| 1235 H19 | 80 | 151 |

Example 3—Coating the Foil

A small amount of 50 micron thick aluminum ribbon (5052 H19) was coated with sorbent and an adhesive, and then embossed with the 16 and 30 TPI embossers. Qualitative observations indicate that the coating was not rubbed off during embossing, except for at the very top point of each embossing (this is acceptable). This method is compared to first embossing the foil with the 16 and 30 TPI embossers, followed by coating the foil with sorbent and adhesive with a spray unit. The order of the coating versus embossing step appears to provide an equivalent coating.

Example 4—Winding Tension

Various pieces of embossed aluminum ribbon were wound around ⅛" and 1/16" diameter mandrels to make approximately 1 cm outside diameter cartridges. Initial winding experiments showed that embossings do not depress or flatten when wound, except in the initial wraps around the mandrel. However, some embossing phasing was observed where the protrusions of the embossings of one wrap would align with the depressions of the embossings of the wrap beneath it, thus creating sections where the two layers of aluminum foil would have no spacing. It was hypothesized that the embossing phasing was due to the variable tension on the ribbon during winding. Better control of the winding was instituted so that a more constant tension winding was obtained. This optimal tension was defined as the maximum tension where no embossing flattening was observed in the inner wraps of the foil, and where no phasing of embossing occurred. The optimal tension was found to be 2.2 N.

Example 5—Embossing Orientation

Cartridges were wound using two different orientations—embossings facing outward and embossings facing inward. All winding was done counter-clockwise as viewed. Hence, in order to have the embossings facing outward from the center pin, the ribbon was aligned with the embossings facing up during winding. To wind cartridges with dimples facing inwards, the ribbon was flipped upside-down, such that the dimples were face-down during winding. From a qualitative perspective, the dimple-outward cartridges were found to have more even spacing of the metal layers.

Example 6—Weld Sealing the Cartridge

A method for sealing wound cartridges was tested in order to eliminate the added diameter of an enclosure. DURAFIX™ aluminum welding rods were purchased to use as solder for sealing the end of the ribbon on the last cartridge winding. To create a smooth exterior to this cartridge, the last few wraps were wound without any embossing of the aluminum. When using 0.003 inch thick aluminum foil, it took approximately 16 inches of ribbon wrapped around the 1/16th inch mandrel to make a half-inch-diameter cartridge. To account for the last few un-embossed wraps, approximately 1.5 inches was not embossed. This method created a smooth "tube" for the cartridge that was sealed using the DURAFIX™ welding rods.

Example 7—Coating the Foil

A 0.5 inch width aluminum ribbon was coated with sorbent on both sides by dip coating, and the wet film thickness was set by wire wound rods that pressed on both sides of the ribbon. The sorbent coating was air dried prior to drying in an oven.

Example 8—Coating the Foil

A 0.5 inch width aluminum ribbon was coated with sorbent on one side. This was achieved by applying the uncured sorbent solution to the foil, followed by drawing a Meyer bar down the length of the foil. After curing, the second side of the foil was coated in a similar manner.

Example 9—Two Different Sorbents on the Same Foil

In order to coat two separate stripes of sorbent onto an aluminum ribbon, portions of the Meyer bar were blocked off, created a narrow segment that divided two layers of sorbent solution. PTFE tape was wrapped around the bar to the spaces between the Meyer bar's wires. The normal, uncoated portion of the Meyer bar was able to spread the solutions on the aluminum, while the PTFE segment prevented spread of adjacent solutions. The sorbent coatings were air dried prior to drying in an oven.

Example 10—Weld Sealing the Cartridge

Cartridges of several different diameters were made using the aluminum ribbon (50 micron 5052-H19). After winding, they were taped shut along the seam. A Tack II resistance welding tool was then used to tack weld the seam closed, after which the tape was removed. Alternatively, the welding tool was used to create an outer casing for the cartridges by tacking the outermost layers together. The ideal settings for tacking created a weld that penetrated 3 to 4 layers of ribbon. These methods created a fairly robust casing for the cartridges, without the weight and added diameter of an aluminum pipe casing.

Example 11—Adhering the Cartridge

A thin layer of AREMCO™ 552 adhesive was applied along the outermost edge of a 1"×3.5" section of coated and embossed ribbon in a wound cartridge. Approximately 100 μL of the adhesive was pipetted onto that edge between the last two layers of ribbon. Wire was wrapped around the entire length of the cartridge and the adhesive was cured in an oven. The cured adhesive was strong enough to seal the cartridge.

Example 12—Partially Embossed Foil

A two-sorbent system was coated onto the aluminum ribbon with the sorbents on flat sections of unembossed ribbon separated by a 0.5 inch section of embossed ribbon. The 3.5 inch wide uncoated ribbon was first embossed in three segments: a central-most 0.5 inch section and a 0.5 inch section along each of the outer-most edges. This step left two parallel unembossed sections of approximately 1 inch width each. A form was applied to the ribbon covering the three embossed sections and allowing sorbent to be airbrush sprayed onto the two flat sections. The first sorbent system, a carbon molecular sieve, was prepared as a solution with adhesive and airbrushed in one unembossed section. The matching section on the opposite side was similarly coated. A heat gun was directed at the coated sections for approximately 25 seconds from a distance of 12 inches.

The hot air was directed up and down the ribbon to ensure an even application of heat along the entire coating length. Next, the second unembossed, uncoated section was coated on both sides with a graphitized carbon sorbent and similarly heated with a heat gun to effect cure. To distinguish between the two sorbent systems, a small corner of ribbon was cut to indicate the bed of carbon molecular sieve. The ribbon was then wound around a mandrel to create the dual-bed cartridge. It was inserted into a thin-wall stainless steel tube to prevent the foil from unwinding.

Example 13—Pressure Drop Testing

Figure 3:
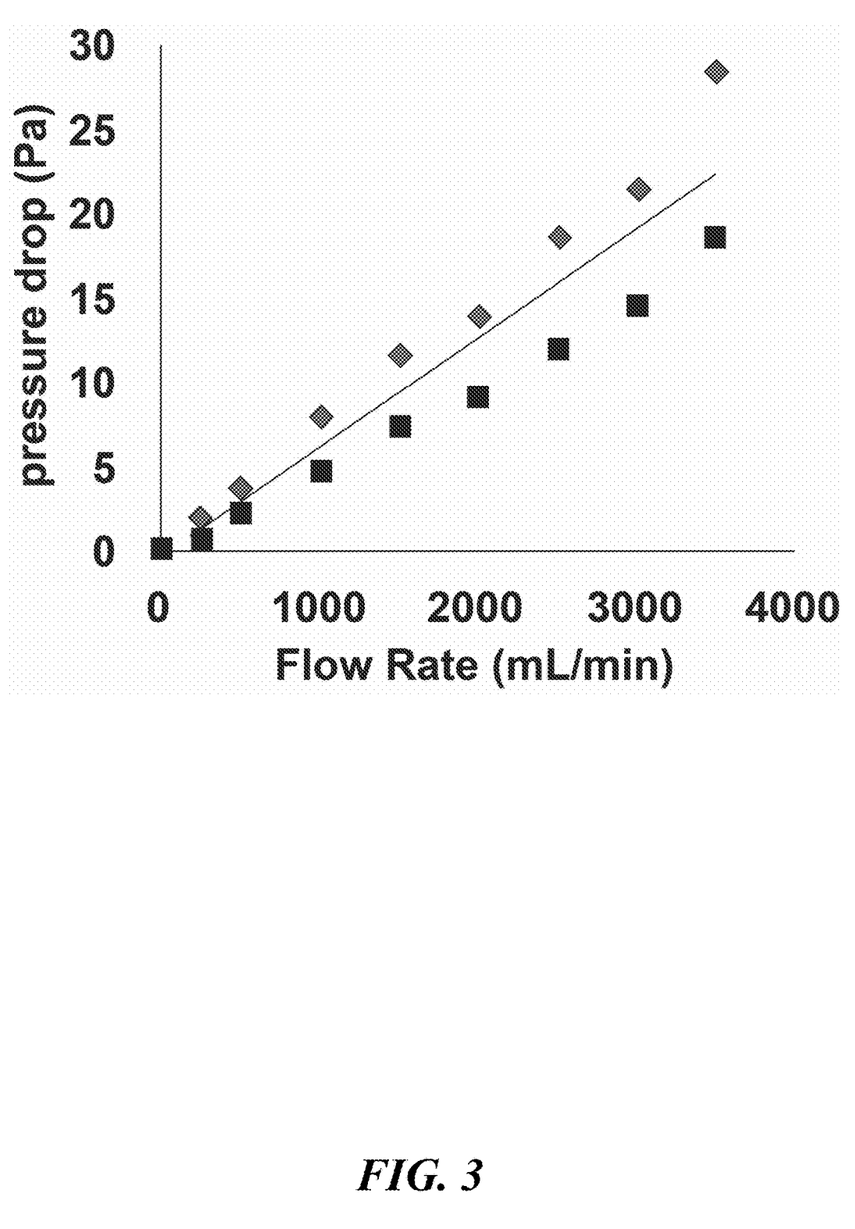
FIG. 3 is a graph of pressure (in Pa) drop as a function of flow rate (in mL/min).

Two cartridges were created from aluminum foil ribbon that was 0.25 inches wide. After embossing and coating with a carbon molecular sieve sorbent, each ribbon was wound and inserted into thin wall stainless steel tubing with an outside diameter of 0.94 inches. The pressure drop across the cartridges in air was measured at flow rates from 0.25-3.5 L/min. The chart in FIG. 3 illustrates that, at air flow rates above 3 L/min, the pressure drop remains less than 30 Pascals.

Example 14—Pressure Drop Comparison

Figure 4:
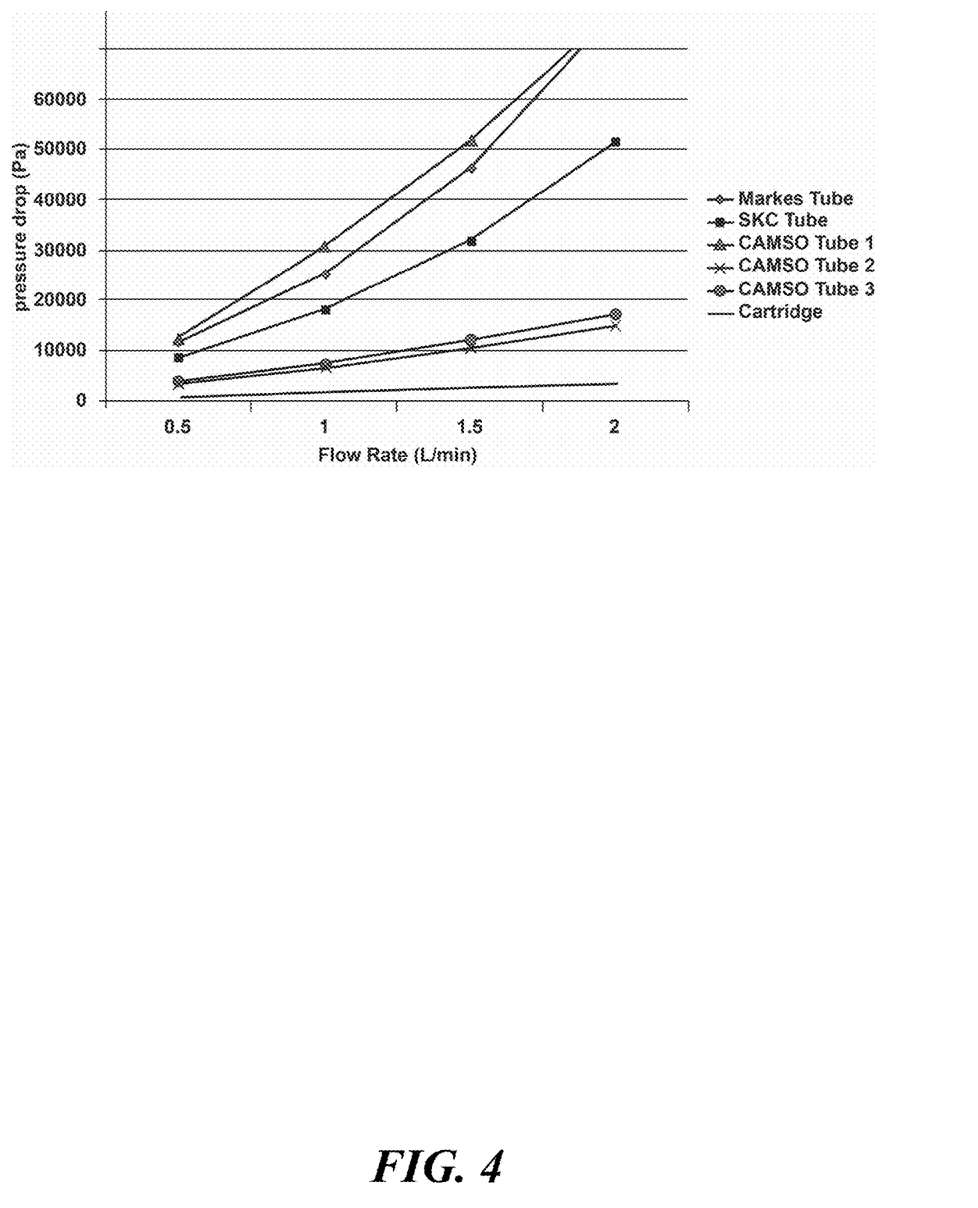
FIG. 4 is a graph of pressure (in Pa) drop as a function of flow rate (in L/min).

The pressure drop of the cartridges as determined in EXAMPLE 13 was compared to a standard sorbent tube. The same coated, embossed foil used for EXAMPLE 13 was instead this time wound into a cartridge just under 0.25 inches in diameter. An emptied, standard commercial stainless steel sorbent tube by Markes was used as the housing for this cartridge. A similar (but un-emptied) Markes packed bed sorbent tube was then used for comparison. As seen in FIG. 4, the cartridge of EXAMPLE 13 has a pressure drop less than 10% that of the commercial tube. Other standard commercial sorbent tubes were also checked at the same flow rates, but and the cartridges made in accordance with the teachings herein exhibited lower pressure drops in all cases.

Example 15—Cartridge as Analyte Collector

Figure 5:
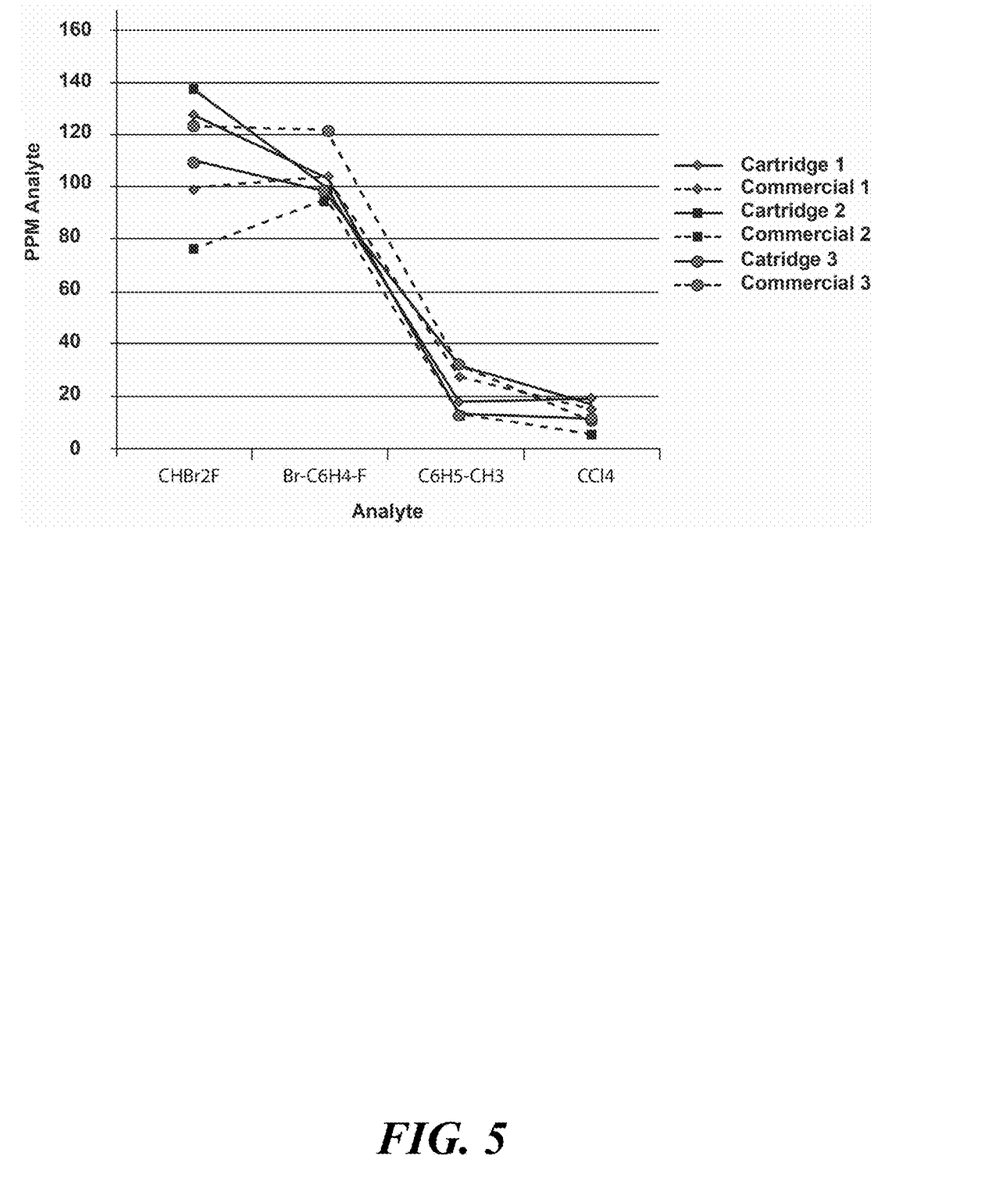
FIG. 5 is a graph of analyte concentration (in PPM) as a function of analyte type.

A dual bed cartridge was created by two separate aluminum ribbons with different sorbents. Ribbon 1 was coated with Carbopack B sorbent, while ribbon 2 was coated with Carboxen 1003. The coated ribbons were then embossed and wound. A traditional stainless steel sorbent tube (3.5×0.25") was emptied of its packed sorbent bed and was used as a common housing tube for both ribbon 1 and ribbon 2. Three cartridges made in accordance with the teachings herein were prepared and directly compared to three commercial cartridges containing traditional packed beds of the same to sorbents. The six cartridges were used to sample the air above potentially polluted soil in order to determine whether halogenated compounds were present in the soil. After collection, the six tubes were thermally desorbed and analyzed by gas chromatography and mass spectrometry. The results are depicted in FIG. 5. As seen therein, the cartridges made in accordance with the teachings herein collect and release analytes very similar to standard commercial sorbent tubes.

Example 19—Cartridge Made From Nickel Alloy

Nichrome Ribbon (80% Ni/20% Cr) of 0.0005 inch thickness, 0.5 inch width, and 6 foot length was embossed using the standard embossing process for aluminum foils. The foil was coated with polyethylene glycol 600 on both sides and would into a cylindrical cartridge. It was contained by placing into a segment of rigid walled aluminum tubing. The cartridge was resistively heated by connecting one electrode to the center of the winding and the other against the aluminum housing, after which 7 volts of DC was passed through the cartridge. A metal temperature of 200° C. was achieved, thus demonstrating the suitability of this cartridge for thermal desorption.

Example 20—Cartridge as Particulate Filter

Approximately 1" wide aluminum foil ribbon was embossed and coated with a multi-micron layer thickness of polyethylene glycol 600 on both sides by wiper bars. The coated foil was wound under tension and slipped into a segment of rigid wall aluminum tubing as containment. The outside diameter of the cartridge was approximately 1 inch. A vacuum pump established a flow rate of 0.9 L/min through the cartridge, and 40 mg of Ashrae Test dust was drawn through the cartridge over approximately 30 seconds. The leading edge of the cartridge was visibly black with the dust. A back-up glass fiber particulate filter consisting of 1 micron pores was inspected and only trace amounts of dust could be seen.

Example 21—Cartridge as Particulate Filter

A vacuum pump was utilized to established a flow rate of 2.7 L/min through a cartridge of the type described in EXAMPLE 20. Next, 40 mg of Ashrae Test dust was drawn through the cartridge over approximately 30 seconds. The leading edge of the cartridge was visibly black with the dust. A back-up glass fiber particulate filter consisting of 1 micron pores was inspected, and an increased level of dust was seen versus the experiment performed at 0.9 L/min. The amount of dust that passed through the cartridge was qualitatively determined to be about 20%.

Various materials may be utilized in the devices disclosed herein. Preferably, these devices include a signature capture media disposed on a substrate film which is thermally and/or electrically conductive. More preferably, the substrate is a film which may be heated for purposes of desorption. Most preferably, the substrate is a film which is sufficiently thermally conductive that it may be resistively or inductively heated for purposes of desorption. The use of metal foils as substrate materials is especially preferred. Such metal foils may comprise aluminum, Inconel, nichrome, steel, or the like. In some embodiments, the metal foil may be laminated to another material such as, for example, paper or plastic films or substrates. In some embodiments, substrates comprising filled polymeric materials may be utilized such as, for example, metal filled polymers.

In many of the systems, devices and methodologies disclosed herein, the substrate material may be heated to effect desorption of signatures. Such heating is preferably in the form of resistive heating, but may also be inductive heating, or heating by hot air or with external sources. In other embodiments, chemical extraction may be utilized to effect signature desorption. In still other embodiments, signatures may be examined or tested in situ.

The signature capture devices utilized in the systems, devices and methodologies disclosed herein may have various shapes or configurations. Preferably, these signature capture devices feature spaced-apart layers that include an embossed substrate having a sorbent or adherent disposed thereon. These spaced-apart layers may be formed by winding the substrate around a mandrel, spindle, spool, or other such device, or by folding or otherwise manipulating the substrate so as to form a multi-layered construct. Such a multi-layered construct may be of any desirable shape, and hence may be circular, elliptical, polygonal or irregular in cross-section.

Figure 6:
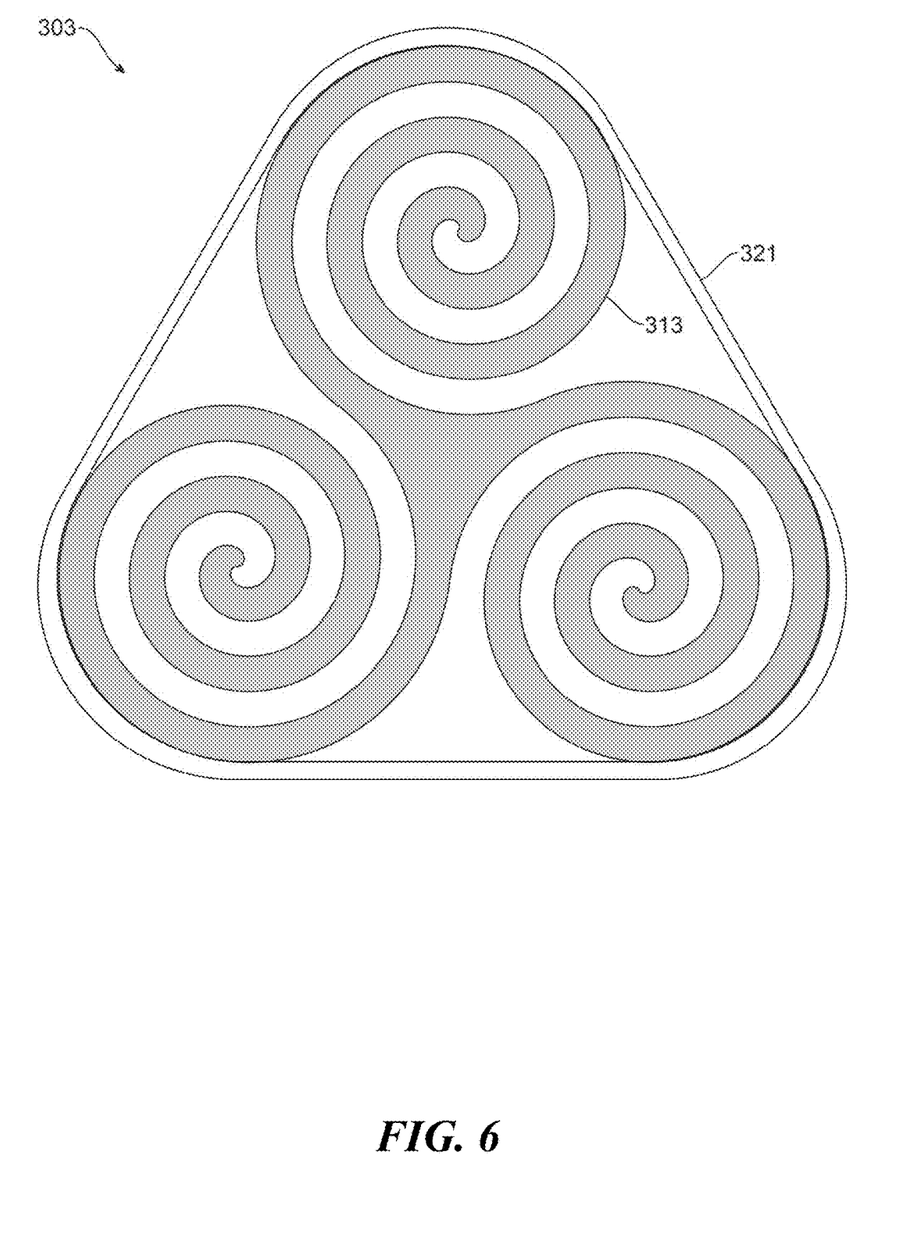
FIG. 6 is an illustration showing the details of another embodiment of a signature collector for use in a sampling device of the type depicted in FIG. 1.

By way of example of the foregoing, FIG. 6 depicts another particular, non-limiting embodiment of a signature collector 303. The details of the substrate 313 have been omitted for ease of illustration, but it will be understood that the substrate may be equipped, for example, with embossments to maintain the layers in a spaced-apart orientation, as well as any absorbents or adherents desired for a target signature. In particular, the substrate 313 in this embodiment may be the same as, or similar to, the substrate 213 of FIG. 2. The substrate 313 in this particular embodiment is disposed in an optional housing 321 to facilitate its handling and may be wound in the depicted configuration through the use of three distinct mandrels (not shown).

While the use of embossments to create layer separation in the multilayered constructs disclosed herein is preferred, one skilled in the art will appreciate that other means may be utilized to achieve a similar end. For example, particulate materials of suitable dimension or diameter may be disposed on the substrate film for this purpose. Alternatively, deposits or transverse ridges of a suitable material (such as, for example, glass fiber, wire or plastic) may be formed on the substrate for this purpose. Similarly, in some embodiments, the substrate may be wound around a comb or other structure to achieve layer separation. In still other embodiments, the substrate or film materials may be chosen to have sufficient moduli such that the film or substrate may be arranged or cast into a multi-layered construct with spaced-apart layers, and will maintain that configuration even upon application of reasonable force.

Various embossments may be utilized in the devices and methodologies disclosed herein. Preferably, these embossments are discrete embossments, and hence do not run the width of the substrate. It is also preferred that the embossments do not create a sine-wave appearance or create parallel passages, as this may reduce flow rates through the spaced-apart layers. The embossments may have various geometries and dimensions, although the use of hemispherical embossments is especially preferred.

Various materials may be utilized as sorbents in the systems, devices and methodologies disclosed herein. These include, without limitation, molecular sieves (including carbon molecular sieves), activated carbon, graphitized carbon black (GCB), silica gel, materials having metal organic frameworks (such as, for example, crystalline metal aluminosilicates which have a three-dimensional interconnecting network of silica and alumina tetrahedra), activated aluminum, diatomaceous earth, and montmorillonites.

Various materials may be utilized as adherents in the systems, devices and methodologies disclosed herein. These include, without limitation, polydimethylsiloxane, mineral oil, siloxane, hydrocarbon oils, polyacrylates, silicone wax, and polyethylene glycol (PEG).

In some embodiments of the systems, devices and methodologies disclosed herein, a sorbent or adherent may be utilized in conjunction with a binder. In some cases, the binder may itself sorb analytes or particles.

Some embodiments of the systems, devices and methodologies disclosed herein may utilize multiple sorbents and/or adherents. These sorbents or adherents may be disposed, for example, as separate deposits or strips on the same substrate, or as intervening layers of distinct composition.

While the devices disclosed herein are preferably active systems, one skilled in the art will appreciate that passive devices may also be constructed in accordance with the teachings herein. Such passive devices do not require the use of a fan or other fluid driving means, but rely instead on ambient fluid flow through the signature capture device. Moreover, both active and passive devices may be made in accordance with the teachings herein which are operable from a variety of platforms. Such platforms include, but are not limited to, carts, ground-based vehicles, aircraft (including drones and gliders), balloons, parachutes, and the like.

The signature capture devices described herein may be equipped with adapters as needed to permit there use with legacy equipment. For example, many models of GS/MS devices are equipped to accept glass or metal tubes of particular diameters for analytical purposes, and these tubes are frequently packed with sorbent beds. In the event that an instance of a signature capture device of the type described herein is disposed in a tube of larger or smaller diameter than a tube size the GS/MS device is configured to accept, adapters of suitable dimensions may be provided to allow the signature capture device to be integrated into such a system.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims.

What is claimed is:

1. A signature collector device for collecting a signature from an ambient fluid, comprising:
    a housing equipped with an inlet and an outlet which are in fluidic communication with each other;
    a wound substrate having a plurality of discrete embossings that maintain adjacent layers of the substrate in a spaced-apart relation to each other, wherein said substrate is disposed in a fluidic flow path between said inlet and said outlet such that the flow path extends through the spaces between adjacent layers in said substrate; and
    an adherent for capturing a signature from an ambient fluid disposed on said substrate such that the adherent is in fluidic contact with said flow path;
    wherein the signature collector device is configured to produce a pressure drop across the device less than 0.01 MPa when an ambient fluid is passed through the device at a flow rate of 1.5 L/min.

2. A method for collecting a signature from an ambient fluid, comprising:
    providing a device comprising (a) a housing equipped with an inlet and an outlet which are in fluidic communication with each other, and (b) a signature collector which has a plurality of spaced-apart layers and which is disposed in a fluidic flow path between said inlet and said outlet such that a flow of fluid passes through adjacent layers of the signature collector, wherein each of the spaced-apart layers includes a substrate having discrete embossments and further having an adherent for capturing a signature from an ambient fluid disposed thereon; and passing the ambient fluid through the device at a flow rate of 1.5 L/min such that the signature is captured by the signature collector;

wherein a pressure drop across the signature collector is less than 0.01 MPa at the flow rate of 1.5 L/min.

3. The method of claim 2, further comprising:
desorbing the signature from the signature collector; and
subjecting the desorbed signature to chemical analysis.

4. The method of claim 2, further comprising:
thermally decomposing the signature, thereby producing thermal decomposition products; and
subjecting the decomposition products to chemical analysis.

5. The method of claim 2, further comprising:
subjecting the signature to at least one action selected from the group consisting of microscopic examination, biological assay and radiological analysis.

6. The method of claim 2, wherein the embossments on a first of the plurality of spaced-apart layers press against a second of the plurality of spaced-apart layers.

7. The method of claim 2, wherein said discrete embossments include a plurality of hemispherical protrusions.

8. The method of claim 2, wherein the substrate has a plurality of particles disposed thereon, and wherein the particles on a first of the plurality of spaced-apart layers press against a second of the plurality of spaced-apart layers.

9. The method of claim 2, wherein the substrate has a plurality of ridges disposed thereon, and wherein the ridges on a first of the plurality of spaced-apart layers press against a second of the plurality of spaced-apart layers.

10. The method of claim 2, wherein the adherent is a sorbent which releasably adsorbs an analyte.

11. The method of claim 10, wherein the sorbent adsorbs the analyte at room temperature, and desorbs the analyte when heated to a temperature within a range of about 60° C. to about 350° C.

12. The method of claim 10, wherein the sorbent adsorbs the analyte at room temperature, and desorbs the analyte when heated to a temperature within a range of about 100° C. to about 300° C.

13. The method of claim 2, wherein said substrate is wound about a mandrel.

14. The method of claim 2, wherein the signature is an analyte, and wherein the analyte is an organic chemical.

15. The method of claim 14, wherein said adherent is a sorbent selected from the group consisting of activated carbon black and molecular sieves.

16. The method of claim 2, wherein the signature is a biological material.

17. The method of claim 2, wherein the signature is a radiological material.

18. The method of claim 2, wherein the signature is a particulate material.

* * * * *